US011141147B2

United States Patent
Mitelberg et al.

(10) Patent No.: US 11,141,147 B2
(45) Date of Patent: Oct. 12, 2021

(54) ENDOSCOPIC SUTURING SYSTEM HAVING EXTERNAL INSTRUMENT CHANNEL

(71) Applicant: Apollo Endosurgery US, Inc., Austin, TX (US)

(72) Inventors: Vladimir Mitelberg, Austin, TX (US); John Mims, Austin, TX (US); Ryan Gilkey, Kyle, TX (US); Landon Gilkey, Austin, TX (US)

(73) Assignee: Apollo Endosurgery US, Inc., Austin, TX (US)

( * ) Notice: Subject to any disclaimer, the term of this patent is extended or adjusted under 35 U.S.C. 154(b) by 615 days.

(21) Appl. No.: 15/468,962

(22) Filed: Mar. 24, 2017

(65) Prior Publication Data

US 2018/0042603 A1 Feb. 15, 2018

Related U.S. Application Data

(63) Continuation-in-part of application No. 15/233,737, filed on Aug. 10, 2016.

(51) Int. Cl.
*A61B 1/00* (2006.01)
*A61B 17/04* (2006.01)
(Continued)

(52) U.S. Cl.
CPC ........ *A61B 17/0469* (2013.01); *A61B 1/0014* (2013.01); *A61B 1/00089* (2013.01);
(Continued)

(58) Field of Classification Search
CPC .......... A61B 17/0469; A61B 2017/047; A61B 2017/0472; A61B 2017/0474;
(Continued)

(56) References Cited

U.S. PATENT DOCUMENTS 3,001,522 A 9/1961 Silverman
3,495,703 A 2/1970 Calabrese
(Continued)

FOREIGN PATENT DOCUMENTS

WO WO 2008/069816 6/2008
WO WO2015052320 A1 4/2015

OTHER PUBLICATIONS

U.S. Appl. No. 61/483,679, filed May 8, 2011, Vladimir Mitelberg.
(Continued)

*Primary Examiner* — Ryan N Henderson
*Assistant Examiner* — Pamela F Wu
(74) *Attorney, Agent, or Firm* — Brian Szymczak

(57) ABSTRACT

A distal cap apparatus for use with an endoscope, having a proximal end and a distal end and a longitudinal axis extending therebetween, includes a mount configured for mounting to the distal end of the endoscope, and a strap connected to the mount and configured for banding about the distal end of the endoscope when the distal end of the endoscope is received in the mount. The mount defines a strap slot configured to receive an end of the strap to configure the strap in the banded configuration. The strap may be elastic. The strap may be a continuous band. In one embodiment, a distal cap apparatus includes a mount having a strap and a buckle for adjusting a size of a loop formed at least partially by the strap about the distal end of the endoscope.

9 Claims, 12 Drawing Sheets

(51) Int. Cl.
*A61B 17/062* (2006.01)
*A61B 90/57* (2016.01)
*A61B 17/06* (2006.01)
A61B 17/00 (2006.01)
A61B 17/30 (2006.01)

(52) U.S. Cl.
CPC ...... *A61B 1/00101* (2013.01); *A61B 1/00137* (2013.01); *A61B 17/0625* (2013.01); *A61B 17/06066* (2013.01); *A61B 90/57* (2016.02); A61B 1/00087 (2013.01); A61B 17/00234 (2013.01); A61B 2017/00292 (2013.01); A61B 2017/00296 (2013.01); A61B 2017/00314 (2013.01); A61B 2017/00349 (2013.01); A61B 2017/00477 (2013.01); A61B 2017/306 (2013.01)

(58) Field of Classification Search
CPC .... A61B 2017/0475; A61B 2017/0477; A61B 2017/0479; A61B 2017/048; A61B 17/0482–0483; A61B 17/0485; A61B 17/0487; A61B 2017/0488; A61B 2017/049; A61B 17/06061; A61B 17/06119; A61B 17/06123; A61B 17/06128; A61B 17/06133; A61B 2017/00292; A61B 2017/00296; A61B 2017/003; A61B 17/00234; A61B 1/00137; A61B 1/0014; A61B 1/0008; A61B 1/00089; A61B 1/00098; A61B 1/00101; A61B 1/00131; A61B 1/00087; A61B 2017/00314; A61B 2017/00349; A61B 2017/00353; A44C 5/00; A44C 5/0053; A44C 5/0061; A44C 5/0069; A44C 5/14; A44C 5/18; A44C 5/185; A44C 5/2071; A44C 5/2076; A44C 5/22; A44B 11/065; A44B 11/125; A44B 11/14; A44B 11/18; A44B 11/20; A44B 11/2557
USPC ................ 600/127, 129, 106–107, 113, 154, 600/175–176
See application file for complete search history.

(56) References Cited

U.S. PATENT DOCUMENTS

| | | | |
|---|---|---|---|
| 3,603,492 A | 9/1971 | Schantz |
| 3,749,328 A | 7/1973 | Dusenbery |
| 3,901,244 A | 8/1975 | Schweizer |
| 4,084,692 A | 4/1978 | Bilweis |
| 4,183,431 A | 1/1980 | Schmidt et al. |
| D263,505 S | 3/1982 | Black |
| 4,794,911 A | 1/1989 | Okada |
| 5,026,379 A | 6/1991 | Yoon |
| 5,041,129 A | 8/1991 | Hayhurst et al. |
| 5,131,534 A | 7/1992 | Brown et al. |
| 5,141,520 A | 8/1992 | Goble et al. |
| 5,196,022 A | 3/1993 | Bilweis |
| 5,217,486 A | 6/1993 | Rice et al. |
| 5,249,671 A | 10/1993 | Sinn |
| 5,263,585 A | 11/1993 | Lawhon et al. |
| 5,284,240 A | 2/1994 | Alpern et al. |
| 5,304,185 A | 4/1994 | Taylor |
| 5,307,924 A | 5/1994 | Manosalva et al. |
| 5,356,424 A | 10/1994 | Buzerak et al. |
| 5,364,408 A | 11/1994 | Gordon |
| 5,403,328 A | 4/1995 | Shallman |
| 5,407,071 A | 4/1995 | Lawhon et al. |
| 5,433,725 A | 7/1995 | Christian et al. |
| 5,437,266 A | 8/1995 | McPherson et al. |
| 5,454,823 A | 10/1995 | Richardson et al. |
| 5,464,424 A | 11/1995 | O'Donnell, Jr. |
| 5,466,241 A | 11/1995 | Leroy et al. |
| 5,470,338 A | 11/1995 | Whitfield et al. |
| 5,474,568 A | 12/1995 | Scott |
| 5,478,344 A | 12/1995 | Stone et al. |
| 5,478,345 A | 12/1995 | Stone et al. |
| 5,514,159 A | 5/1996 | Matula et al. |
| 5,520,702 A | 5/1996 | Sauer et al. |
| 5,527,321 A | 6/1996 | Hinchliffe |
| 5,545,180 A | 8/1996 | Le et al. |
| 5,573,496 A | 11/1996 | McPherson et al. |
| 5,575,800 A | 11/1996 | Gordon |
| 5,584,860 A | 12/1996 | Goble et al. |
| 5,584,861 A | 12/1996 | Swan et al. |
| 5,601,557 A | 2/1997 | Hayhurst |
| 5,626,590 A | 5/1997 | Wilk |
| 5,626,614 A | 5/1997 | Hart |
| 5,628,395 A | 5/1997 | Daniele et al. |
| 5,643,320 A | 7/1997 | Lower et al. |
| 5,649,940 A | 7/1997 | Hart et al. |
| 5,653,717 A | 8/1997 | Ko et al. |
| 5,662,588 A | 9/1997 | Iida |
| 5,662,658 A | 9/1997 | Wenstrom, Jr. |
| 5,669,917 A | 9/1997 | Sauer et al. |
| 5,681,331 A | 10/1997 | De La Torre et al. |
| 5,685,823 A | 11/1997 | Ito et al. |
| 5,690,655 A | 11/1997 | Hart et al. |
| 5,700,272 A | 12/1997 | Gordon et al. |
| 5,707,379 A | 1/1998 | Fleenor et al. |
| 5,713,910 A | 2/1998 | Gordon et al. |
| 5,720,766 A | 2/1998 | Zang et al. |
| 5,733,293 A | 3/1998 | Scirica et al. |
| 5,741,277 A | 4/1998 | Gordon |
| 5,755,729 A | 5/1998 | De la Torre et al. |
| 5,765,740 A | 6/1998 | Ferguson |
| 5,782,862 A | 7/1998 | Bonutti |
| 5,792,152 A | 8/1998 | Klein et al. |
| 5,792,153 A | 8/1998 | Swain et al. |
| 5,810,848 A | 9/1998 | Hayhurst |
| 5,814,054 A | 9/1998 | Kortenbach et al. |
| 5,814,071 A | 9/1998 | McDevitt et al. |
| 5,817,013 A | 10/1998 | Ginn et al. |
| 5,819,918 A | 10/1998 | Scanlon |
| 5,824,009 A | 10/1998 | Fukuda et al. |
| 5,833,055 A | 11/1998 | Cerwin et al. |
| 5,843,099 A | 12/1998 | Nichols et al. |
| 5,860,992 A | 1/1999 | Daniel et al. |
| 5,879,371 A | 3/1999 | Gardiner et al. |
| 5,887,594 A | 3/1999 | LoCicero, III |
| 5,891,160 A | 4/1999 | Williamson, IV et al. |
| 5,897,563 A | 4/1999 | Yoon et al. |
| 5,897,564 A | 4/1999 | Schulze et al. |
| 5,910,105 A | 6/1999 | Swain et al. |
| 5,918,733 A | 7/1999 | Cerwin et al. |
| 5,944,739 A | 8/1999 | Zlock et al. |
| 5,947,982 A | 9/1999 | Duran |
| 5,951,587 A | 9/1999 | Quereshi et al. |
| 5,954,731 A | 9/1999 | Yoon |
| 5,954,732 A | 9/1999 | Hart et al. |
| 5,954,733 A | 9/1999 | Yoon |
| 5,964,764 A | 10/1999 | West, Jr. et al. |
| 5,993,466 A | 11/1999 | Yoon |
| 5,993,467 A | 11/1999 | Yoon |
| 6,010,525 A | 1/2000 | Bonutti et al. |
| 6,036,699 A | 3/2000 | Andreas et al. |
| 6,048,351 A | 4/2000 | Gordon et al. |
| 6,053,935 A | 4/2000 | Brenneman et al. |
| 6,068,648 A | 5/2000 | Cole et al. |
| 6,071,233 A | 6/2000 | Ishikawa et al. |
| 6,071,289 A | 6/2000 | Stefanchik et al. |
| 6,077,286 A | 6/2000 | Cuschieri et al. |
| 6,086,600 A | 7/2000 | Kortenbach |
| 6,086,601 A | 7/2000 | Yoon |
| 6,086,608 A | 7/2000 | Ek et al. |
| 6,095,323 A | 8/2000 | Ferguson |
| 6,096,051 A | 8/2000 | Kortenbach et al. |
| 6,117,144 A | 9/2000 | Nobles et al. |
| 6,126,666 A | 10/2000 | Trapp et al. |
| 6,135,385 A | 10/2000 | Martinez de Lahidalga |
| 6,136,010 A | 10/2000 | Modesitt et al. |

(56) References Cited

U.S. PATENT DOCUMENTS

| | | |
|---|---|---|
| RE36,974 E | 11/2000 | Bonutti |
| 6,149,658 A | 11/2000 | Gardiner et al. |
| 6,159,234 A | 12/2000 | Bonutti et al. |
| 6,171,316 B1 | 1/2001 | Kovac et al. |
| 6,224,614 B1 | 5/2001 | Yoon |
| 6,277,064 B1 | 8/2001 | Yoon |
| 6,277,132 B1 | 8/2001 | Brhel |
| 6,293,961 B2 | 9/2001 | Schwartz et al. |
| 6,306,081 B1 | 10/2001 | Ishikawa |
| 6,312,448 B1 | 11/2001 | Bonutti |
| 6,352,503 B1 | 3/2002 | Matsui et al. |
| 6,358,259 B1 | 3/2002 | Swain et al. |
| 6,443,962 B1 | 9/2002 | Gaber |
| 6,467,612 B1 | 10/2002 | Rosenfeld |
| 6,475,230 B1 | 11/2002 | Bonutti et al. |
| 6,533,795 B1 | 3/2003 | Tran et al. |
| 6,533,796 B1 | 3/2003 | Sauer et al. |
| 6,569,085 B2 * | 5/2003 | Kortenbach ....... A61B 1/00073 600/104 |
| 6,585,744 B1 | 7/2003 | Griffith |
| 6,596,001 B2 | 7/2003 | Stormby et al. |
| 6,635,073 B2 | 10/2003 | Bonutti |
| 6,656,182 B1 | 12/2003 | Hayhurst |
| 6,663,639 B1 | 12/2003 | Laufer et al. |
| 6,663,641 B1 | 12/2003 | Kovac et al. |
| 6,663,643 B2 | 12/2003 | Field et al. |
| 6,695,852 B2 | 2/2004 | Gleason |
| 6,699,183 B1 | 3/2004 | Wimmer |
| 6,719,763 B2 | 4/2004 | Chung et al. |
| 6,719,764 B1 | 4/2004 | Gellman et al. |
| 6,733,509 B2 | 5/2004 | Nobles et al. |
| 6,740,030 B2 | 5/2004 | Martone et al. |
| 6,755,843 B2 | 6/2004 | Chung et al. |
| 6,804,937 B2 | 10/2004 | Dey et al. |
| 6,808,491 B2 | 10/2004 | Kortenbach et al. |
| 6,866,673 B2 | 3/2005 | Oren et al. |
| 6,893,393 B2 | 5/2005 | Carillo |
| 6,896,686 B2 | 5/2005 | Weber |
| 6,921,361 B2 | 7/2005 | Suzuki et al. |
| 6,921,408 B2 | 7/2005 | Sauer |
| 6,923,819 B2 | 8/2005 | Meade et al. |
| 6,955,643 B2 | 10/2005 | Gellman et al. |
| 6,966,916 B2 | 11/2005 | Kumar |
| 6,988,985 B2 | 1/2006 | Suzuki et al. |
| 6,988,987 B2 | 1/2006 | Ishikawa et al. |
| 6,997,931 B2 | 2/2006 | Sauer et al. |
| 7,033,370 B2 | 4/2006 | Gordon et al. |
| 7,033,379 B2 | 4/2006 | Peterson |
| 7,041,111 B2 | 5/2006 | Chu |
| 7,048,755 B2 | 5/2006 | Bonutti et al. |
| 7,060,025 B2 | 6/2006 | Long et al. |
| 7,060,077 B2 | 6/2006 | Gordon et al. |
| 7,063,710 B2 | 6/2006 | Takamoto et al. |
| 6,986,737 B2 | 7/2006 | Suzuki et al. |
| 7,070,044 B2 | 7/2006 | Rosenfeld |
| 7,083,630 B2 | 8/2006 | DeVries et al. |
| 7,083,638 B2 | 8/2006 | Foerster |
| 7,087,012 B2 | 8/2006 | Ishibiki |
| 7,090,686 B2 | 8/2006 | Nobles et al. |
| 7,090,690 B2 | 8/2006 | Foerster et al. |
| 7,094,246 B2 | 8/2006 | Anderson et al. |
| 7,112,208 B2 | 9/2006 | Morris |
| 7,131,979 B2 | 11/2006 | DiCarlo et al. |
| 7,144,401 B2 | 12/2006 | Yamamoto et al. |
| 7,147,652 B2 | 12/2006 | Bonutti et al. |
| 7,150,757 B2 | 12/2006 | Fallin et al. |
| 7,153,314 B2 | 12/2006 | Laufer et al. |
| 7,175,636 B2 | 2/2007 | Yamamoto et al. |
| 7,179,277 B2 | 2/2007 | Cunningham |
| 7,191,900 B2 | 3/2007 | Opie et al. |
| 7,198,599 B2 | 4/2007 | Goto et al. |
| 7,204,802 B2 | 4/2007 | De Leval |
| 7,220,266 B2 | 5/2007 | Gambale |
| 7,223,230 B2 | 5/2007 | Zirps et al. |
| 7,235,086 B2 | 6/2007 | Sauer et al. |
| 7,264,624 B2 | 9/2007 | Nash et al. |
| 7,318,802 B2 | 1/2008 | Suzuki et al. |
| 7,322,161 B2 | 1/2008 | Prescott |
| 7,326,221 B2 | 2/2008 | Sakamoto et al. |
| 7,338,504 B2 | 3/2008 | Gibbens, III et al. |
| 7,344,545 B2 | 3/2008 | Takemoto et al. |
| 7,371,215 B2 | 5/2008 | Colliou et al. |
| 7,431,694 B2 | 10/2008 | Stefanchik et al. |
| 7,445,603 B2 | 11/2008 | Zimmon |
| 7,527,590 B2 | 5/2009 | Suzuki et al. |
| 7,566,300 B2 | 7/2009 | Devierre et al. |
| 7,575,548 B2 | 8/2009 | Takemoto et al. |
| 7,601,161 B1 | 10/2009 | Nobles et al. |
| 7,637,369 B2 | 12/2009 | Kennedy et al. |
| 7,665,279 B2 | 2/2010 | Prescott |
| 7,703,459 B2 | 4/2010 | Saadat et al. |
| 7,727,144 B2 | 6/2010 | Suzuki |
| 7,766,162 B2 | 8/2010 | Maki et al. |
| 7,775,973 B2 | 8/2010 | Okada et al. |
| 7,776,066 B2 | 8/2010 | Onuki et al. |
| 7,785,348 B2 | 8/2010 | Kuhns et al. |
| 7,918,867 B2 | 4/2011 | Dana et al. |
| 7,931,661 B2 | 4/2011 | Saadat et al. |
| 7,935,128 B2 | 5/2011 | Rioux et al. |
| 7,988,656 B2 | 8/2011 | Uesugi et al. |
| 8,016,840 B2 | 9/2011 | Takemoto et al. |
| 8,021,376 B2 | 9/2011 | Takemoto et al. |
| 8,287,556 B2 | 10/2012 | Gilkey et al. |
| 8,679,136 B2 | 3/2014 | Mitelberg |
| 9,198,562 B2 | 12/2015 | Mitelberg et al. |
| 9,486,126 B2 | 11/2016 | West et al. |
| 2002/0040227 A1 | 4/2002 | Harari et al. |
| 2002/0087190 A1 | 7/2002 | Benavitz et al. |
| 2003/0176762 A1 | 9/2003 | Kammerer |
| 2003/0176880 A1 | 9/2003 | Long et al. |
| 2003/0181924 A1 | 9/2003 | Yamamoto et al. |
| 2004/0015177 A1 | 1/2004 | Chu |
| 2004/0249393 A1 | 12/2004 | Weisel et al. |
| 2005/0065401 A1 | 3/2005 | Saadat et al. |
| 2005/0149067 A1 | 7/2005 | Takemoto et al. |
| 2005/0250984 A1 | 11/2005 | Lam et al. |
| 2005/0250985 A1 | 11/2005 | Saadat et al. |
| 2006/0281970 A1 | 12/2006 | Stokes et al. |
| 2006/0282093 A1 * | 12/2006 | Shelton, IV ......... A61B 1/0014 606/144 |
| 2007/0197862 A1 * | 8/2007 | Deviere ............. A61B 1/00087 600/102 |
| 2008/0039255 A1 | 2/2008 | Jinno et al. |
| 2008/0045979 A1 | 2/2008 | Ma |
| 2009/0236399 A1 * | 9/2009 | Bilotti .................. A61B 17/072 227/180.1 |
| 2009/0312775 A1 | 12/2009 | Gilkey et al. |
| 2010/0036198 A1 | 2/2010 | Tacchino et al. |
| 2010/0048988 A1 * | 2/2010 | Pastorelli ........... A61B 1/00087 600/104 |
| 2010/0298630 A1 | 11/2010 | Wingall |
| 2011/0099773 A1 | 5/2011 | Golden et al. |
| 2012/0271327 A1 | 10/2012 | West et al. |
| 2013/0006287 A1 | 1/2013 | West et al. |
| 2014/0343358 A1 * | 11/2014 | Hameed ............. G02B 23/2423 600/109 |
| 2016/0045197 A1 | 2/2016 | Mitelberg et al. |

OTHER PUBLICATIONS

U.S. Appl. No. 61/495,970, filed Jun. 11, 2011, Vladimir Mitelberg.
U.S. Appl. No. 61/073,340, filed Jun. 17, 2008, J. Landon Gilkey.
U.S. Appl. No. 61/162,249, filed Mar. 20, 2009, J. Landon Gilkey.
U.S. Appl. No. 15/233,737, filed Aug. 10, 2016, Vladimir Mitelberg.
U.S. Appl. No. 13/327,988, filed Dec. 16, 2011, Steven West et al.
U.S. Appl. No. 13/539,661, filed Jul. 2, 2012, Steven West et al.

* cited by examiner

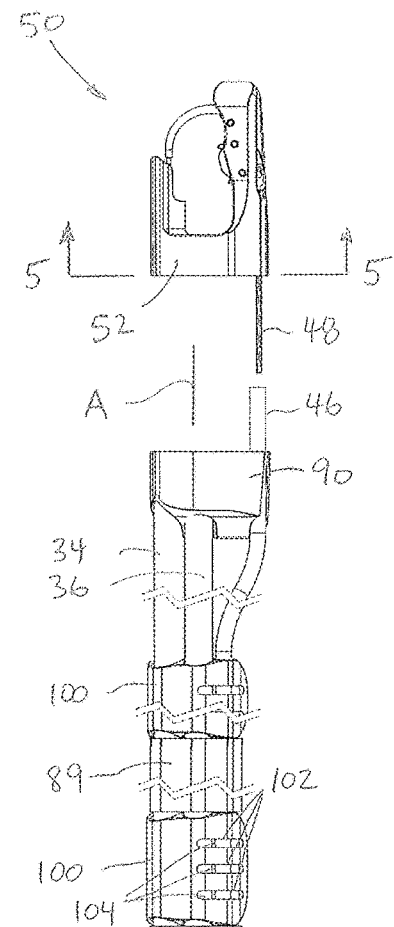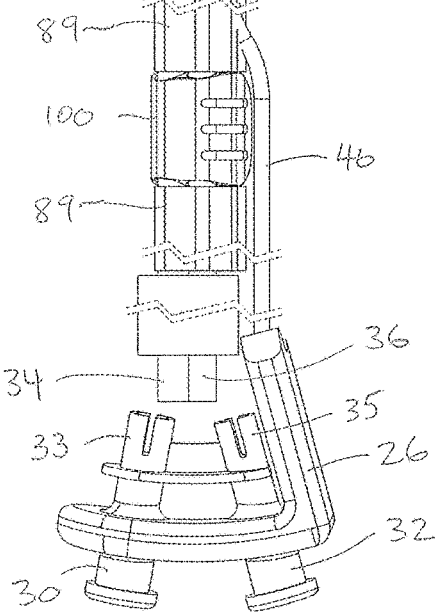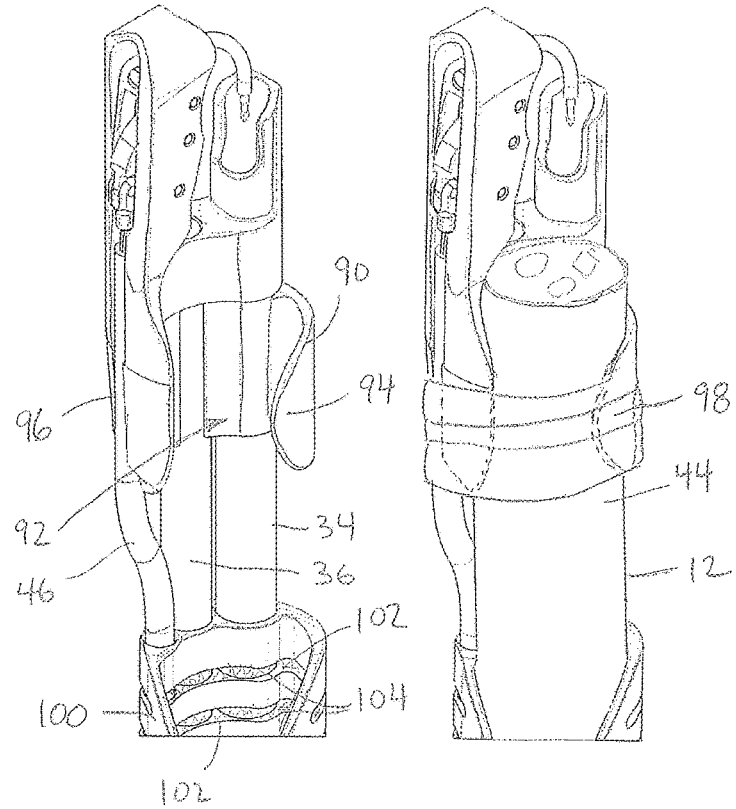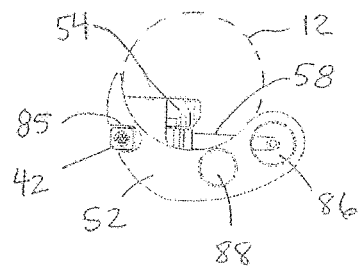

ENDOSCOPIC SUTURING SYSTEM HAVING EXTERNAL INSTRUMENT CHANNEL

CROSS-REFERENCE TO RELATED APPLICATIONS

This application is a continuation-in-part of U.S. Ser. No. 15/233,737, filed Aug. 10, 2016, which is hereby incorporated by reference herein in its entirety.

This application is related to U.S. Pat. Nos. 8,287,556, 8,679,136, and 9,198,562, which are hereby incorporated by reference herein in their entireties.

This application is also related to U.S. Ser. No. 13/327,988, filed Dec. 16, 2011, Ser. No. 13/539,661, filed Jul. 2, 2012, and Ser. No. 13/539,777, filed Jul. 2, 2012, all of which are hereby incorporated by reference herein in their entireties.

BACKGROUND

1. Field

The present invention relates to a treatment device which can be inserted into a body through a natural orifice with an endoscope or other steerable guide member. The present invention may be used to perform suturing on the tissue of a mammal, whether human or not, and whether or not alive, but is not limited thereto.

2. State of the Art

U.S. Pat. No. 7,344,545 to Takemoto discloses an endoscopic suturing system having many embodiments to perform a surgical operation. This suturing system generally comprises an assembly having first and second arms which are actuatable by a push rod to rotatably approach each other while one arm grasps tissue and the second arm drives a curved needle through the tissue. The system also includes a needle recovery member requiring a rigid alignment with the curved needle arm. While this system affords the ability to grasp thick tissue, the tissue grasping arm and the arrangement of the needle recovery member provides bulk to the system making it difficult to use in endoscopic procedures.

Co-owned U.S. Pat. No. 8,287,556 to Gilkey et al. describes a system that addresses various limitations of the system by Takemoto. Gilkey describes an endoscopic treatment device having a structure enabling a small profile for delivery while providing an end effector with both a wide opening and closing angle that produces the large needle force for piercing tissue to perform a surgical operation such as tissue approximation and suturing within the body.

The Gilkey system comprises a transmission assembly coupled to a proximal handle assembly for operation outside of the body and a distal cap assembly where the cap assembly is adapted to engage the distal end of an endoscope. The transmission assembly is connected to a link mechanism and is actuated to cause a needle assembly having a needle holder arm and needle coupled to the cap assembly to move in a direction to puncture tissue and a direction to be removed from tissue. The endoscope to which the cap assembly is coupled has first and second instrument channels to receive cooperative devices therethrough. The first device is positioned within the first instrument channel of the endoscope and has a distal end adapted to receive and grasp the needle and a proximal end coupled to a handle assembly. The second device is positioned within the second instrument channel of the endoscope to engage tissue, and draw the tissue back into the path of the needle so that the tissue can be pierced by the needle as the needle is moved from an open to a closed position.

While the Gilkey system works very well, it presently requires association with an endoscope having two instrument channels. This may limit use of the system to larger endoscopes with such features. However, smaller endoscopes are gaining favor. Such smaller endoscopes, with their smaller profile, can be more easily advanced through a natural orifice. However, the reduced profile of the smaller endoscopes cannot accommodate the two instrument channels required for the Gilkey suturing system.

SUMMARY

An endoscopic suturing system includes an endoscope, a suturing device, a needle assembly movable through tissue by the suturing device, and first and second devices used in association with the suturing device.

In accord with an embodiment, the endoscope can be a small profile endoscope, generally 5-10 mm in diameter, and can have one or more instrument channels, and optionally no instrument channel. As such, the number of instrument channels is not critical to operation of the system. The endoscope includes a distal end and a proximal end.

The suturing device includes a distal cap assembly adapted to be mounted at the distal end of the endoscope, and transmission assembly extending between the cap assembly and a proximal handle adapted to apply a force to the transmission assembly and operate the cap assembly remotely from the distal cap assembly. The cap assembly includes a mount, a support bracket extending distally from the mount, and a needle arm rotatably mounted on the bracket. A bell crank is also rotatably mounted on the support bracket and engages the needle arm. The distal end of the transmission assembly is attached to the bell crank, such that when the transmission assembly is operated by the handle, movement of the bell crank causes rotation of the needle arm between the open and closed positions. The needle assembly includes a needle body, a needle tip with a tissue-piercing end, and suture coupled to the needle body. The needle arm couples to the needle assembly at the needle body.

In accord with one aspect of the embodiment, the mount of the cap assembly also includes a first throughbore and a second throughbore. The first throughbore is positioned in alignment with the needle arm and needle when the needle arm is in the closed position. A needle guide extends distally from over the first throughbore. The second throughbore is positioned between the first throughbore and the support bracket. The mount is structured such that when the cap assembly is coupled to the endoscope, the first and second throughbores are positioned radially outside the profile of the endoscope. In accord with another aspect of the embodiment, the cap is coupled to the distal end of the endoscope with a peripheral engagement structure in the form of a resilient cap clip integrated with the mount.

First and second lumen, each including a distal end and a proximal end, extend from the first and second throughbores, respectively, external of the endoscope, to the proximal handle. The distal end of the first lumen is fixed in the first throughbore, and its proximal end is coupled to a first connector on the handle. The distal end of the second lumen is fixed in the second throughbore, and its proximal end is coupled a second connector on the handle. The first and second lumen may be defined by discrete catheters or integrated into a common catheter. The catheters or catheter may be covered in a common sheath.

The first lumen is adapted to receive a first device that has a distal end effector that can receive and grasp the needle. The second lumen is adapted to receive a second device that has a distal end effector that can engage tissue, and draw the tissue back into the path of the needle so that the tissue can be pierced by the needle as the needle is moved from an open to a closed position.

A plurality of ancillary clips are provided about the first and second lumen and transmission assembly to couple them to the endoscope. The ancillary clips are longitudinally spaced apart along the lumens and transmission assembly to allow suitable flexure and operation of the first and second devices extending within the first and second lumen, as well as operation of the transmission assembly.

The proximal handle includes a lever operated handle coupled to the transmission assembly for operating the transmission assembly, a bracket including first and second ports communicating with the respective first and second connectors coupled to the first and second lumen, and a collar that attaches the handle to the endoscope.

In accord with another embodiment, substantially similar to the suturing system described above, the cap includes a peripheral engagement structure in the form of a rotatable arm integrated with the mount that captures the endoscope.

In use, the suturing device is coupled to an endoscope and prepared for use. In so coupling, the cap assembly is attached to the distal end of the endoscope, with the cap clip or rotatable arm being opened to laterally receive the endoscope, and then closed to secure the cap assembly and endoscope relative to each other. The first and second lumen and transmission assembly are coupled along the endoscope with the supplemental clips. The collar is properly positioned at the handle of the endoscope. The first device is advanced through the first port, into the first lumen and to the cap assembly. A needle assembly is loaded onto the needle arm.

The distal end of the endoscope and cap assembly of the suturing device are advanced into a natural orifice of a patient, optionally through a guide tube, and approached to target tissue. The handle of the suturing device is operated to move the needle arm into the open position. The end effector of the second device is advanced through the second port, into the second lumen, and beyond the cap assembly. The end effector of the second device is operated to engage tissue and the second device is retracted to draw the tissue in a fold into the path of the needle. The handle is then operated to move the needle arm into the closed position, piercing the tissue fold and passing the suture through the tissue fold during the movement. As the needle enters the closed position, it is securely engaged by the end effector of the first device. The handle is then operated to move the needle arm toward the open position, thereby disengaging the needle arm from the needle. The end effector of the second device is released from the tissue. The endoscope is then moved or operated to displace the cap assembly relative to the sutured tissue fold. The needle and suture may be secured onto the tissue, such as by knotting or cinching, or the needle may be repositioned in engagement with the needle arm and additional suture loops may be formed within adjacent or other areas of tissue. Once the suturing is complete, the needle arm is returned to a closed position, and the endoscope and suturing device are removed from the patient.

The suturing assembly is then released from over the endoscope by releasing the peripheral engagement structure and ancillary clips from over the endoscope and releasing the collar from over the endoscope.

The suturing assembly is adapted for use with an endoscope that does not necessarily have at least two instrument channels. As such, the suturing system can be used with an endoscope independent of the number of instrument channels it contains. Also the suturing system is adapted to not be limited by the size of an endoscope, and can even be used with the smaller endoscopes that are available in many surgical settings and which can be more easily advanced through a natural orifice.

In accord with another embodiment, a distal cap apparatus for use with an endoscope, having a proximal end and a distal end and a longitudinal axis extending therebetween, includes a mount configured for mounting to the distal end of the endoscope, and at least one strap connected to the mount and configured for banding about the distal end of the endoscope when the distal end of the endoscope is received in the mount. The mount defines at least one strap slot configured to receive an end of each strap to position the strap in the banded configuration.

Preferably, the strap is elastic. The strap slot may be dimensioned to compress the strap when the strap is in the strap slot. The strap may be frictionally engaged in the strap slot to retain the strap positioned relative to the strap slot. The mount may define a cutting blade slot and a blade bearing surface. The cutting blade slot extends longitudinally in a direction intersecting with a pathway of the strap in the strap slot. The blade bearing surface extends in a plane at a fixed angle that intersects with a plane of the strap in the strap slot. A cutting blade can be inserted into the cutting blade slot parallel to the blade bearing surface to cut the strap and prevent orientation of the blade in a manner that would damage the endoscope.

The mount may have a locking tab that extends into the strap slot and is configured to engage with the strap when the strap is in the strap slot. The strap may have a plurality of teeth and grooves that engage the locking tab when the strap is moved through the slot. The locking tab may be configured to permit the strap to move in only one direction through the strap slot.

In accord with yet another embodiment a distal cap apparatus for use with an endoscope, having a proximal end and a distal end and a longitudinal axis extending therebetween, includes a mount configured for mounting to the distal end of the endoscope, and a strap connected to the mount and configured to be banded about the endoscope in a banded configuration. The mount includes a buckle configured for adjusting a size of a loop defined by the strap and the mount when the strap is in the banded configuration. The strap may be a continuous band, and the strap may be elastic.

The buckle may be fixed to the mount. The buckle may define a serpentine strap pathway through which the strap is routed when the strap is in the banded configuration. The buckle may be moveable relative to the mount, and the buckle is moveable between an open and a closed configuration.

The buckle may be pivotally coupled to the mount. In one embodiment, one end of the band is secured to the buckle and another end of the band is secured to the mount. In one embodiment, when the buckle is moved from the closed position to the open position the buckle is pivoted away from the mount to increase the size of the loop, and when the buckle is moved from the open position to the closed position the buckle is pivoted toward the mount to decrease the size of the loop. In one embodiment, a first end of the strap is removably connected to the buckle and a second end of the strap is secured to the distal cap assembly.

In one embodiment, the buckle has a plurality of connections each of which is configured for selective connection to the second end of the strap. Also, in one embodiment, when the buckle is moved from the closed position to the open position the buckle is pivoted away from the mount to increase the size of the loop, and when the buckle is moved from the open position to the closed position the buckle is pivoted toward the mount to decrease the size of the loop.

BRIEF DESCRIPTION OF THE DRAWINGS

FIG. 3 is a broken side elevation view of a suturing device of the endoscopic suturing system of FIG. 1.

FIG. 5 is a cross-section view through line 5-5 in FIG. 3.

FIG. 6 is a perspective view of the distal end of the suturing device of FIG. 3.

FIG. 7 is a view similar to FIG. 6 shown in combination with an endoscope.

DETAILED DESCRIPTION OF THE PREFERRED EMBODIMENTS

With reference to the following description, the terms "proximal" and "distal" are defined in reference to the hand of a user of the device, with the term "proximal" being closer to the user's hand, and the term "distal" being further from the user's hand such as to often be located further within a body of the patient during use.

Figure 1:
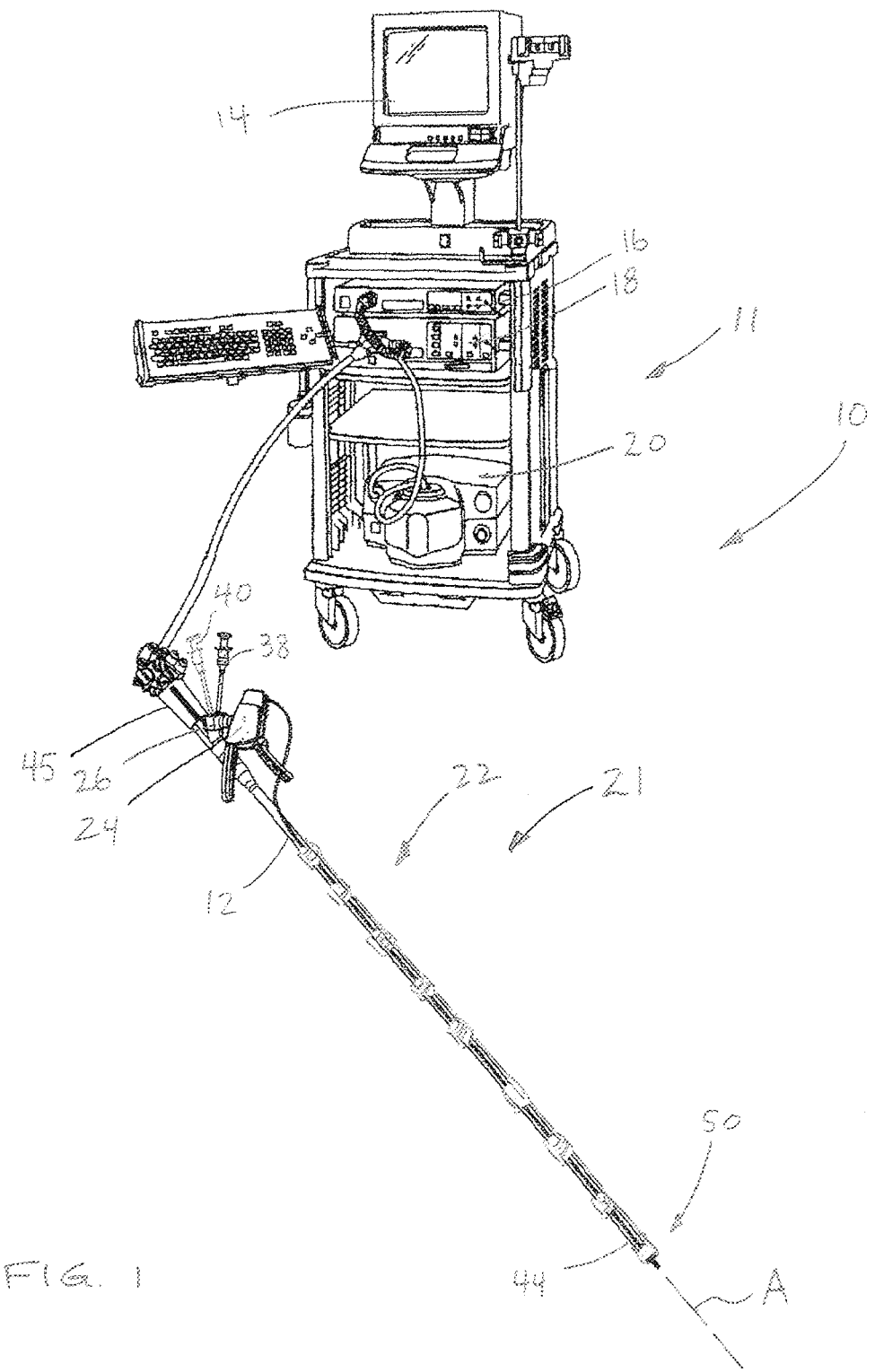
FIG. 1 is a perspective view of an endoscopic suturing system according an embodiment of the invention.
Figure 4:
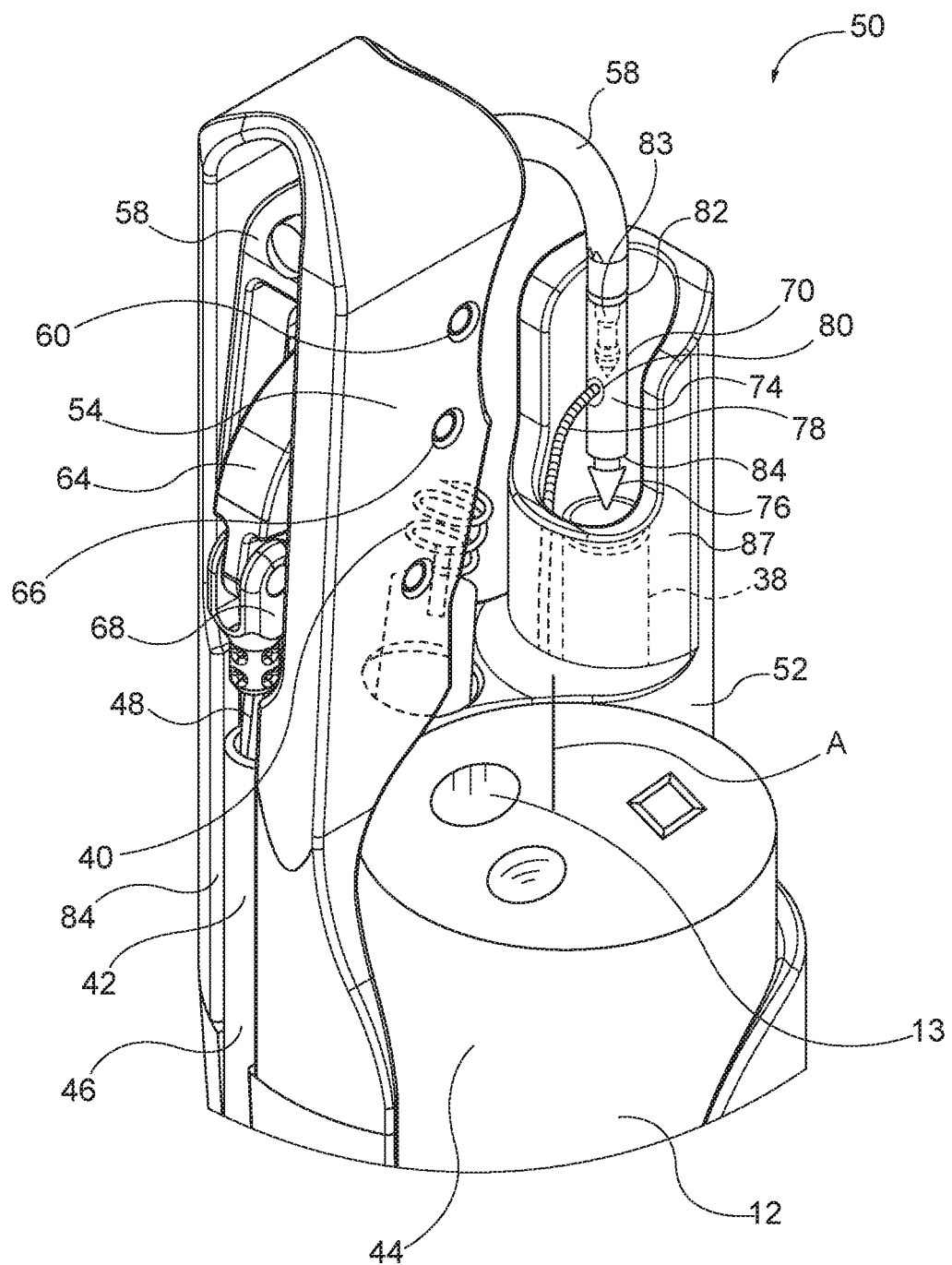
FIG. 4 is a perspective distal end view of an embodiment of a cap assembly attached at the distal end of an endoscope of the endoscope suturing system.

Referring to FIG. 1, an endoscopic treatment system 10 includes an endoscope system 11 and an endoscopic suturing system 22. The endoscope system 11 includes an endoscope 12, a video display unit 14, an image processing device 16, a light source 18, and a suction device 20. In accord with an embodiment, the endoscope 12 has a small profile, generally 5-10 mm in diameter. However, the size of the endoscope is not critical, and elements described herein can be adapted for endoscopes of other sizes. In the embodiment shown, the endoscope 12 has a single instrument channel 13 (FIG. 4). However, the endoscope may have more than one instrument channel or no instrument channel all, as operation of the system does not necessarily require use of the instrument channel through the endoscope. The endoscope 12 includes a distal end 44 and a proximal end 45 and a longitudinal axis A extending therebetween.

Figure 2:
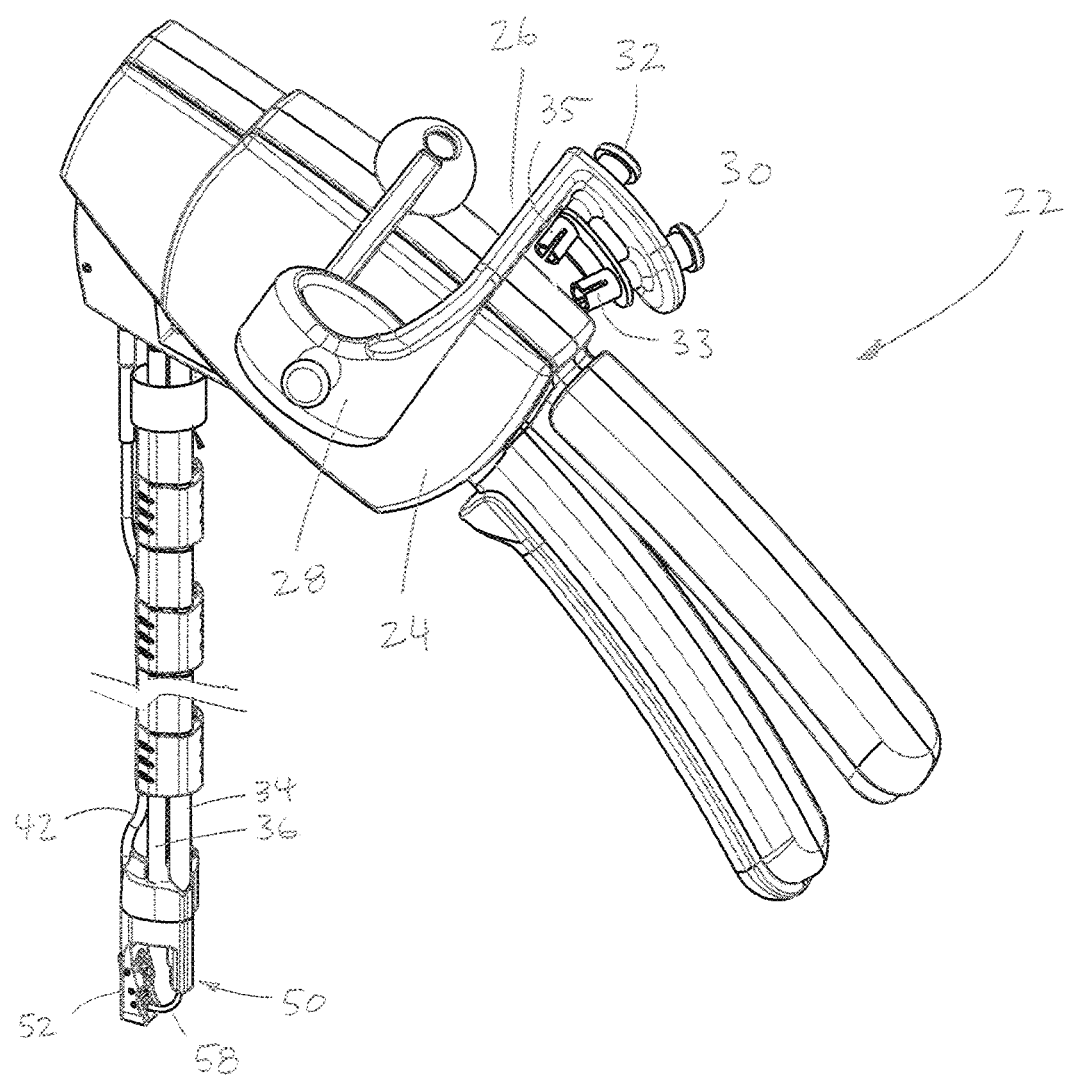
FIG. 2 is a proximal perspective view of a suturing device of the endoscopic suturing system of FIG. 1.

The suturing system 21 includes a suturing device 22 (FIG. 2), a needle assembly 70 (FIG. 4) movable through tissue by the suturing device 22, and first and second devices 38, 40 used in association with the suturing device 22 (FIGS. 2 and 4).

Referring to FIGS. 2 and 3, the suturing device 22 has a proximal operable handle 24 provided with a mounting bracket 26 and a collar 28 at which the handle is removably coupled to endoscope 12. The bracket 26 includes first and second instrument ports 30, 32 at which instruments can be received into first and second lumen 34, 36, respectively. First and second tubular connectors 33, 35 are aligned with the ports 30, 32 that couple the ports 30, 32 to the first and second lumen 34, 36.

A transmission assembly 42 includes a transmission sheath 46 and a transmission cable 48 displaceable within the transmission sheath 46, both coupled relative to the handle 24. The transmission sheath 46 is coupled relative to a first portion of the handle (i.e., a stationary member), and the transmission cable 48 is coupled to a second portion of the handle (i.e., a movable lever), such that when the handle 24 is operated the cable 48 is displaced within the transmission sheath 46.

The first and second lumens 34, 36 and the transmission assembly 42 extend from the proximal handle 24, along the outside of the endoscope 12, to a distal cap assembly 50. The distal cap assembly 50 is adapted to be mounted at the distal end 44 of the endoscope 12, and the handle 24 remotely operates the cap assembly 50 via the transmission assembly 42.

Referring to FIG. 4, the cap assembly 50 includes a mount 54, U-shaped support bracket 54 extending distally from the mount, and a needle arm 58 rotatably mounted on the bracket 52 with a first pin 60. A bell crank 64 is rotatably mounted at a second pin 66 on the support bracket 54 and engages the needle arm 58 at intermeshing gears (not shown). The distal end of the transmission cable 48 of the transmission assembly 42 is attached to the bell crank 64 at a clevis 68. When the transmission assembly 42 is operated by the handle 24, it results in rotation of the bell crank 64 and consequent rotation of the needle arm 58 between the open and closed positions.

The needle assembly 70 is coupled to a needle mount 83 at an end of the needle arm 58. The needle assembly 70 includes a tubular needle body 74, a needle tip 76, and suture 78 coupled to the needle body. The needle body 74 includes a side opening 80 through which the suture 78 extends, a first end 82 at which the needle assembly is coupled to the needle mount 83, and a second end 84 to which the tip 76 is coupled. The tip 76 defines a tissue-piercing taper. The suture 78 may be formed of any materials commonly available for surgical suture such as nylon, polyolefins, PLA, PGA, stainless steel, nitinol and others. One suitable needle assembly is described in more detail in previously incorporated U.S. Pat. No. 9,198,562.

Turning to FIG. 5, the mount 52 of the cap assembly 50 also includes a side recess 85 into which the transmission assembly 42 is received, and a first throughbore 86 and a second throughbore 88. The first throughbore 86 is positioned in alignment with both the needle mount 83 of the needle arm 58 and needle assembly 70 when the needle arm 58 is in the closed position. A tissue guide 87 extends distally on the mount 52 from over the first throughbore 86 and provides a surface on which to stabilize tissue as it is pierced by the needle assembly 70. The second throughbore 88 is positioned between the first throughbore 86 and the support bracket 54. More particularly, the axial center of the second throughbore 88 is positioned between the first throughbore 86 and the pin 60 (or axis) on which the end effector rotates. The first and second throughbores 86, 88 may be parallel to each other and the longitudinal axis A of the endoscope, or the second throughbore 88 may be obliquely angled relative to the first throughbore 86 so as to direct the second device 40 at a particular orientation into the needle path, as described further below. The mount 52 is structured such that when the cap assembly 50 is coupled to the endoscope 12, as described below, the first and second throughbores 86, 88 are positioned radially outside the profile of the endoscope.

Referring to FIGS. 3 and 5, the distal end of the first lumen 34 is fixed in the first throughbore 86, and its proximal end is coupled to a first connector 33 on the handle bracket 26. The distal end of the second lumen 36 is fixed in the second throughbore 88, and its proximal end is coupled the second connector 35 on the handle bracket 26. The first and second lumen 34, 36 may be defined by discrete catheters (as shown in FIGS. 3 and 6) or may be defined as separate lumen of a common catheter. Further, the catheters 34, 36 (or common catheter) may be covered in a common sheath 89 along at least a portion of their lengths. The common sheath 89 may extend along the entire length of the catheters 34, 36, a partial length, or may be provided in sections along selected portions of the catheters 34, 36.

Turning to FIGS. 1, 3, 4 and 6, the first lumen 34 is adapted to receive a first device 38 that has a distal end effector that can receive and grasp the needle assembly 70. The second lumen 36 is adapted to receive a second device 40 that has a distal end effector that can engage tissue, and draw the tissue back into the path of the needle so that the tissue can be pierced by the needle assembly 70 as the needle assembly is moved from the open to the closed position.

The cap assembly 50 is secured to the distal end 44 of the endoscope 12 with a peripheral engagement structure that is adapted to be positioned about greater than 180° of the circumference of the distal end of the endoscope. In one embodiment, the structure is a cap clip 90 provided in abutting relationship to the mount, and preferably integrated with the mount 52. The clip 90 includes an opening 92, and an arm 94 that may be resiliently deformed to allow the distal end 44 of the endoscope 12 access through the opening 92 and then released to capture the distal end of the endoscope within the clip. The clip 90 may be formed from ABS plastic, other suitable plastics, elastic materials, as well as polymer-coated metals. The distal end of the clip 90 abuts against the proximal end of the mount 52. The first and second lumen 34, 36 extend within the clip 90, and a peripheral recess 96 is provided in the clip to receive the transmission assembly in a relatively flush configuration. A tape or cohesive banding 98 may be used over the clip 90 and distal end 44 of the endoscope to additionally secure the cap assembly relative to the endoscope during use. By way of example, a surgical-grade tape or silicone cohesive banding may be used.

Referring to FIGS. 3 and 6, a plurality of ancillary clips 100 are provided about the first and second lumen 34, 36 and transmission assembly 42 and forming a body that is adapted to extend greater than 180° about the circumference of the endoscope 12. The clips are adapted to secure the first and second lumen 34, 36 and transmission assembly 42 at various displaced locations to the endoscope 12. The ancillary clips 100 include transverse slots 102 that may be filled with a material or an adhesive 104, such as a polymer and optionally silicone. The filling material 104 has a higher coefficient of friction than the body of the clip to enhance the grip of the clip about the endoscope. The ancillary clips 100 are longitudinally spaced apart along the lumens 34, 36 and transmission assembly 42 to allow suitable flexure and operation of the first and second devices 38, 40 extending within the first and second lumen 34, 36, as well as flexure and operation of the transmission assembly 42. The spaced apart ancillary clips 100 may be interposed with portions of the common sheath 89.

In light of the above, the suturing device may be prepared for use in conjunction with an endoscope as follows. The cap assembly 50 is attached to the distal end 44 of the endoscope 12, with the cap clip 90 being opened to laterally receive the endoscope, and then released to secure the cap assembly 50 and endoscope 12 relative to each other. The first and second lumen 34, 36 and transmission assembly 42 are coupled along the endoscope 12 with the ancillary clips 100. The collar 28 is properly positioned at the proximal handle 45 of the endoscope 12. The first device, a needle capture instrument 38 loaded with a needle assembly 70, is advanced through the first port 32, into the first lumen 34 and to the cap assembly 50. Suitable needle capture devices 38 are described in detail in previously incorporated U.S. Pat. No. 8,679,136. The needle assembly 70 is loaded onto the needle arm 58, with the suture 78 extending parallel to the needle capture instrument 38 within the first lumen 34.

Figure 8:
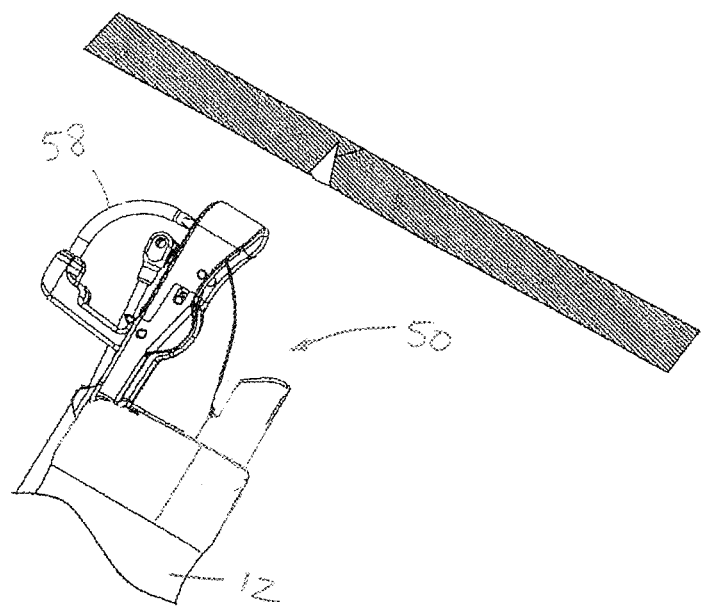
FIGS. 8-12 illustrate use of the endoscopic suturing system to endoscopically suture tissue.
Figure 9:
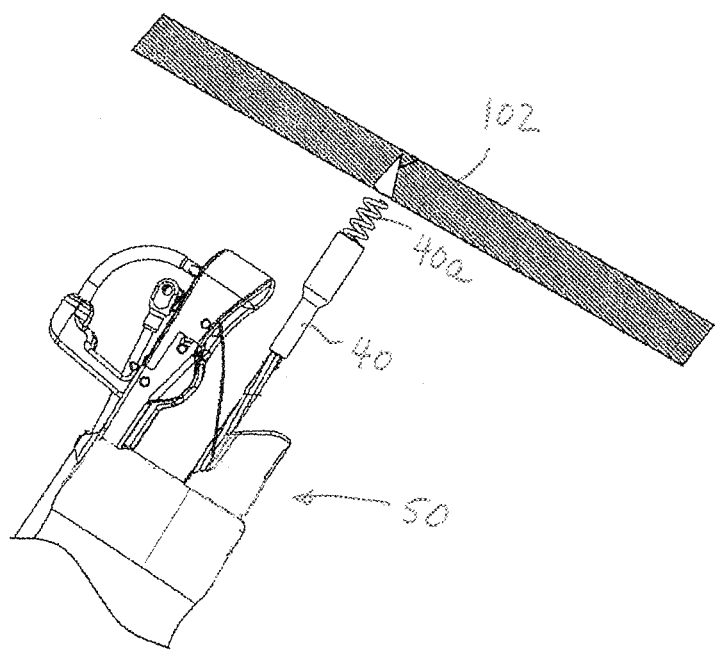
Figure 10:
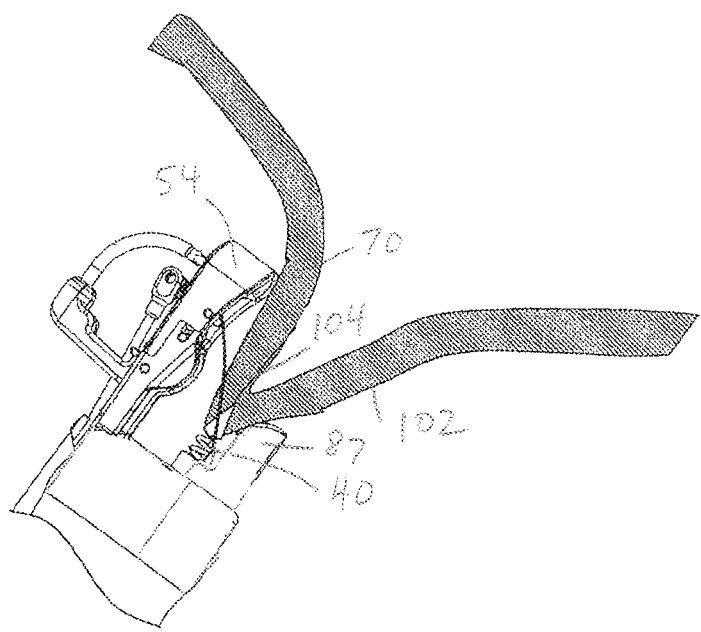
Figure 11:
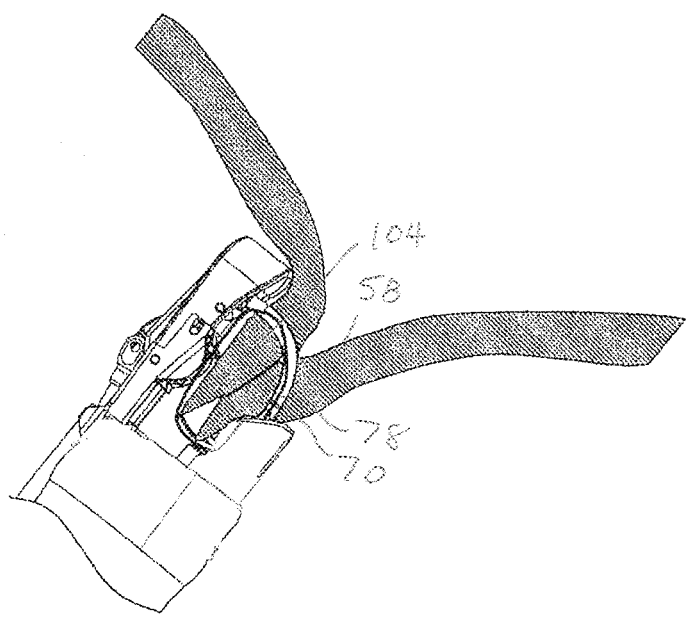
Figure 12:
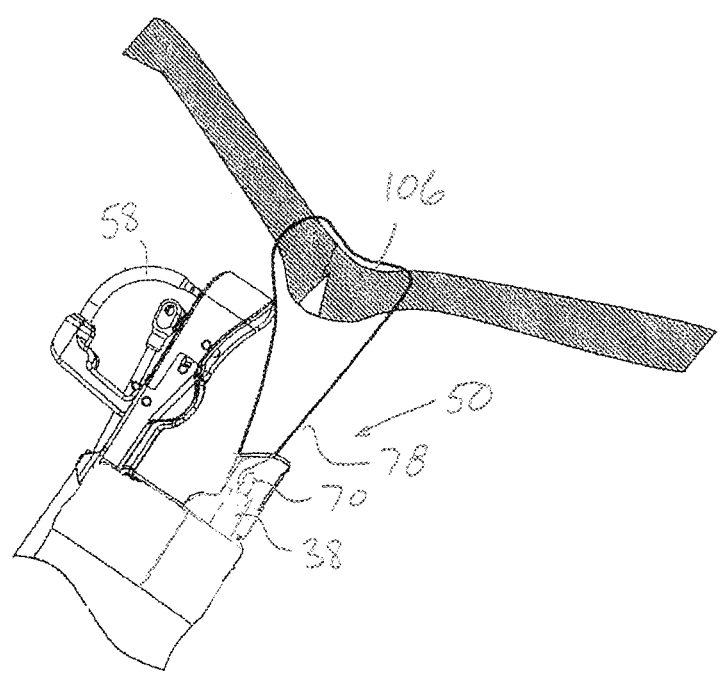

With reference to FIGS. 1 and 8, the distal end of the endoscope 12 and cap assembly 50 of the suturing device 22 are advanced into a natural orifice of a patient, optionally through a guide tube (not shown), and approached to target tissue 102. The handle 24 of the suturing device 22 is operated to move the needle arm 58 into the open position, as shown in FIG. 8. Turning to FIG. 9, the end effector of the second device, e.g., a tissue retractor 40 having a helical coil 40a at its distal end, is advanced through the second port 32, into the second lumen 36 (FIG. 3) and out the second throughbore 88 (FIG. 5), and beyond the cap assembly 50. Suitable tissue retractor instruments are described in detail in previously incorporated U.S. Ser. No. 13/539,661. Other tissue retractors, including forceps, may also be used. The helical coil 40a is operated to engage target tissue 102. The tissue retractor 40 is withdrawn to draw the tissue 102 against the tissue guard 87 and into a fold 104 located within the path of the needle assembly 70; i.e., between the bracket 54 and needle guide 87, as shown in FIG. 10. The orientation of the second throughbore 88, either parallel or obliquely angled relatively to the first throughbore 86, is adapted to guide the tissue retractor to engage and retract tissue into the needle path. The handle 24 is then operated to move the needle arm 58 into the closed position, thereby piercing the tissue fold 104 and passing the needle assembly 70 with suture 78 through the tissue fold during the movement. When the needle arm 58 is in the closed position, the needle is received within the distal end of the needle capture device 38 (FIG. 4). The needle capture device 38 is operated to securely engage the needle 70. The handle 26 is then operated to move the needle arm 58 toward the open position, thereby disengaging the needle arm 58 from the needle assembly 70, which remains in the needle capture device 38 (FIG. 12). The tissue retractor 40 is also released from the tissue and withdrawn back through the second lumen 36. The endoscope 12 is then moved to displace the cap assembly 50 relative to the sutured tissue 106. The needle 70 and suture 78 may be secured onto the tissue, such as by knotting or cinching, or the needle may be repositioned on the needle arm and additional suture loops may be formed within adjacent or other areas of tissue. Once the suturing is complete, the needle arm 58 is returned to a closed position, and the endoscope 12 and suturing device 22 are removed from the patient.

The suturing assembly is then released from over the endoscope by releasing the cap clip and ancillary clips from over the endoscope 12 and releasing the collar 28 from the proximal end of the endoscope.

Figure 13:
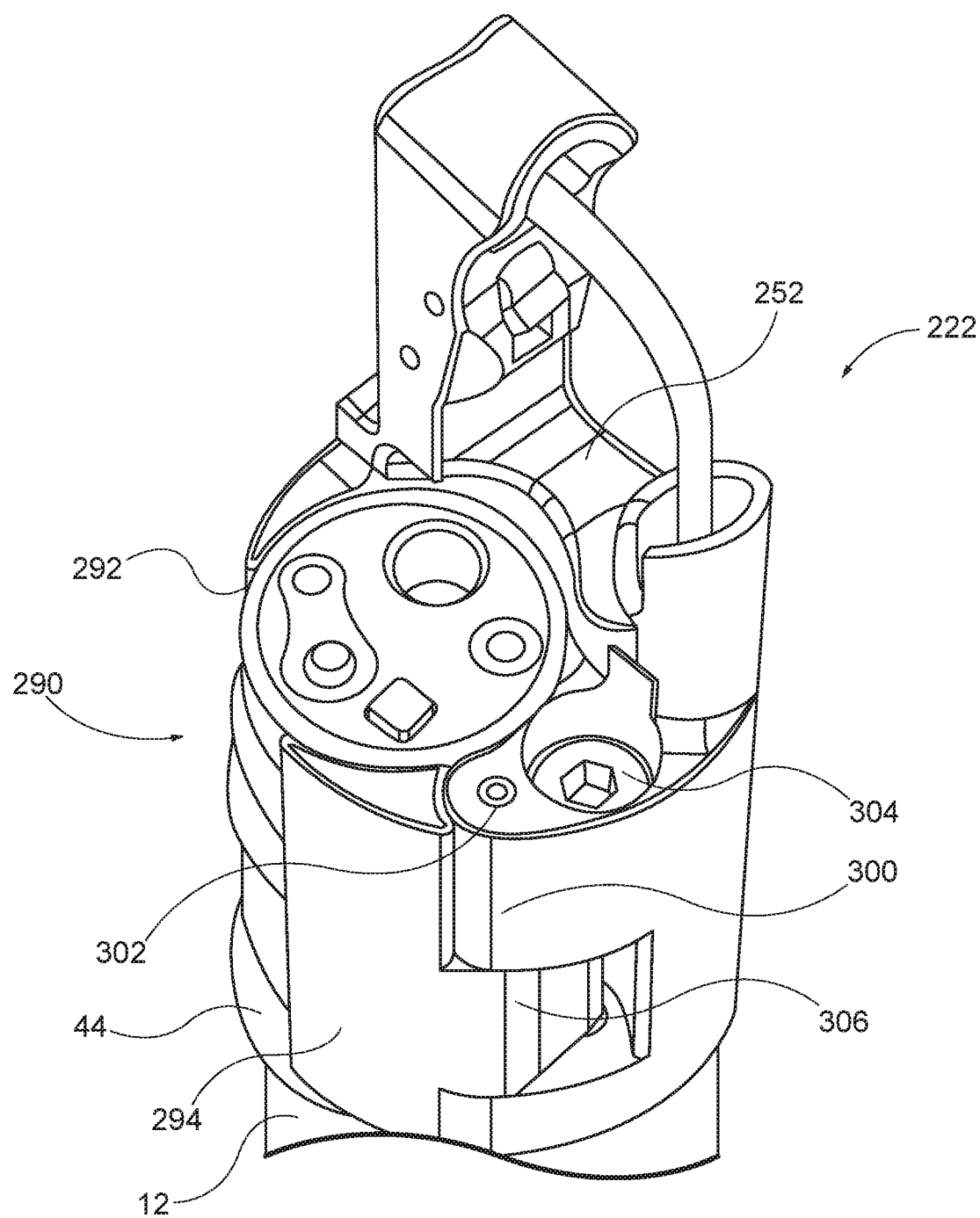
FIG. 13 is a perspective distal end view of another embodiment of a cap assembly attached at the distal end of an endoscope of the endoscope suturing system.

Turning now to FIG. 13, another embodiment of a suturing system 222 is shown that is substantially similar to suturing system 22 described above but which includes variations on the peripheral engagement structure. In distinction from the cap clip 90 with resilient arm 94 of the earlier embodiment, the suturing system 222 includes an engagement structure 290 defined by a recess 292 (indicated at the location of the distal end 44 of the endoscope 12) and an independently rotatable arm 294 that is structured to retain the endoscope within the recess when in a closed position. The arm 294 is mounted at a hinge 300 on a hinge pin 302, and can be rotated open to allow insertion of the distal end 44 of the endoscope 12 into the recess, and then rotated closed to secure the endoscope by the arm 294. The arm 294 may be associated with a lock that when released allows relatively free rotation of the arm 294 on its hinge 300 and when locked fixes the position of the arm 294. The lock may be defined by a set screw 304 that is rotated into and out of engagement with a portion 306 of the hinge 300. Alternatively, the set screw 304 may operate as a cam on the hinge or other portion of the arm to rotate the arm 294 into a closed position as the set screw 304 is rotated in a one direction, and a release on the cam as the set screw is rotated in the opposite direction. Other cam structures can also be used. As yet another alternative, the arm 294 may be biased with a spring located, by way of example, at the hinge 300 and which automatically forces the arm 294 toward a closed position to secure the endoscope once the endoscope is positioned within the recess 294. The arm 294 may be integrated with the mount 252, or may be provided in an abutting relationship.

Figure 14:
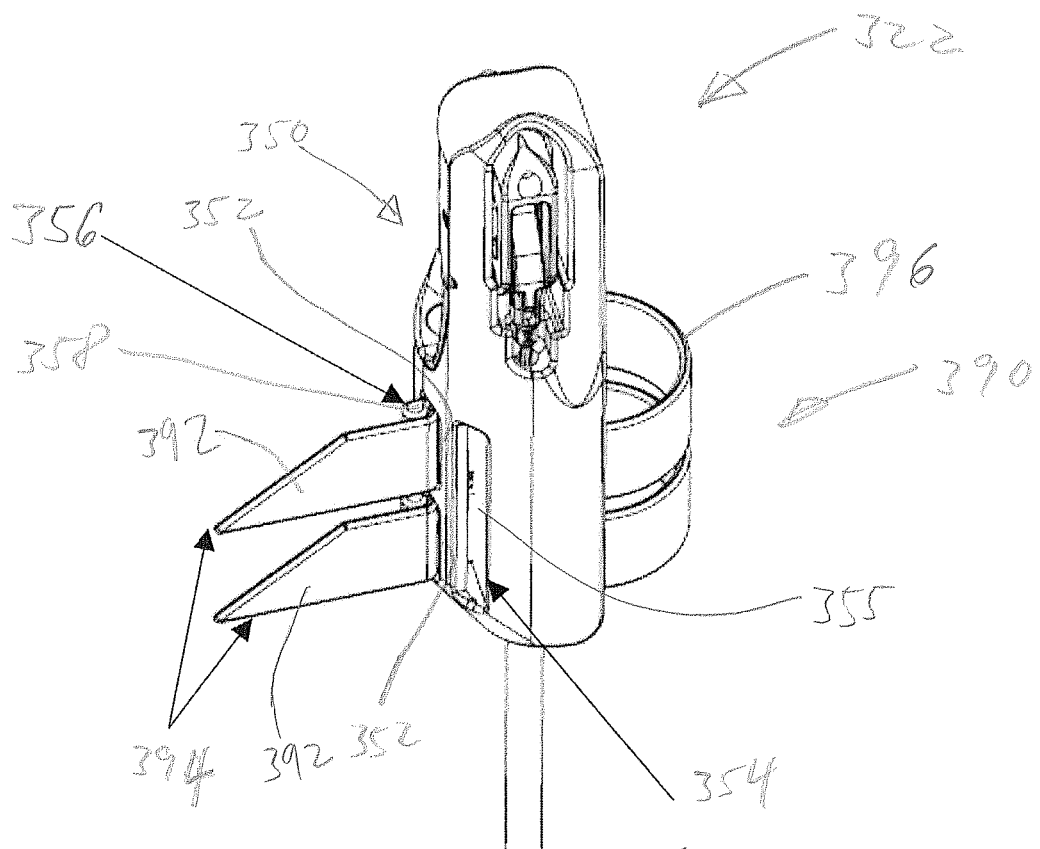
FIG. 14 is a perspective distal end view of another embodiment of a cap assembly that is configured for attachment at the distal end of an endoscope of the endoscope suturing system.
Figure 15:
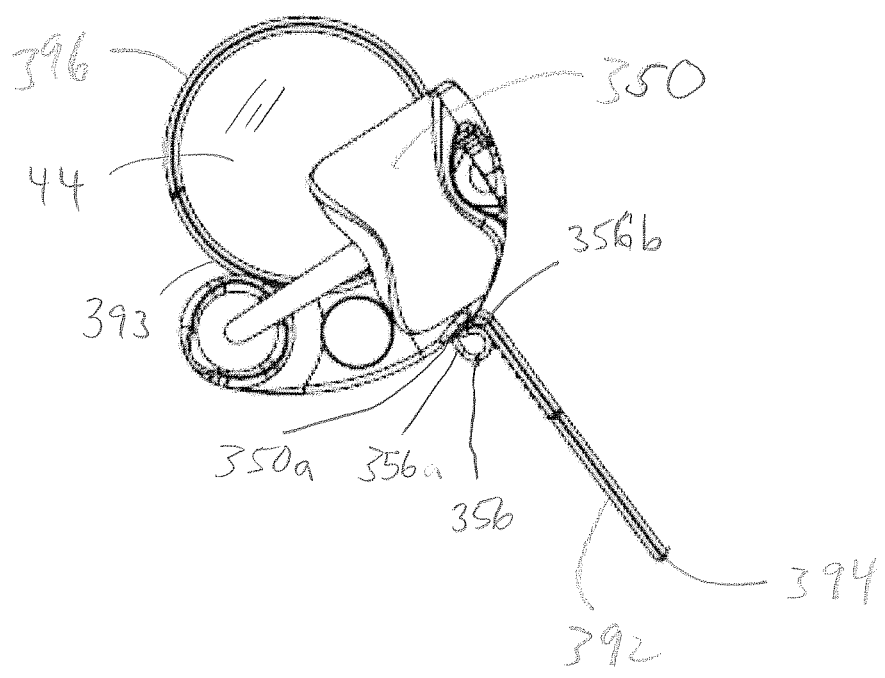
FIG. 15 is a top plan view of the cap assembly of FIG. 14

Turning now to FIGS. 14 and 15, another embodiment of a suturing system 322 is shown that is substantially similar to suturing system 22 described above, but which includes variations on the peripheral engagement structure. In distinction from the cap clip 90 with resilient arm 94 of the earlier embodiment, the suturing system 322 includes a cap apparatus 390 defined by at least one and preferably a plurality of straps 392 that are structured to retain the distal end 44 (FIG. 15) of the endoscope adjacent a cap mount 350. The straps 392 are preferably elastic and may be formed from silicone rubber or similar material. The cap mount 350 defines at least one strap engaging slot 352 corresponding to the at least one straps 392. For each strap 392, one end 393 is secured to the cap assembly 350 near the strap engaging slot 352, while another end 394 is configured to pass through the slot 352 to form a loop 396. The strap engaging slot 352 and the strap 392 are configured to provide resistance to pulling the strap 392 through the slot 352. Thus, when the end 394 of the strap 392 is pulled through the slot 352, resisted thereby, and the strap 392 is released, the loop 396 formed by the strap 392 will be maintained without the strap 392 having to be tightened. In one embodiment, the width of the slot 352 is made slightly smaller than the thickness of the corresponding strap 392 passing through the slot 352 so that when the strap 392 is in the slot 352 the strap 352 will be compressed and frictionally engaged by the slot 352.

Also, in the embodiment shown in FIGS. 14 and 15, a wedge 356 is attached to the mount 350 by a hinge pin 358. The wedge 356 has a teardrop profile shown more clearly in FIG. 15. A first side 356*a* of the wedge 356 is configured to engage a shoulder 350*a* of the mount 350 when the wedge 356 is in a closed position, as shown in FIG. 15. When the wedge 356 is in the closed position, the strap 392 contacts a second side 356*b*, as shown in FIG. 15. When the strap 392 is pulled through the slot 352 from the closed position of the wedge 356, the strap 392 frictionally engages the wedge 356 to rotate it clockwise in FIG. 15 and in a direction away from the shoulder 350*a*. The rotation of the wedge 356 causes a tip of the wedge 356 to move away from the shoulder 350*a* into a pathway of the strap 392, which further compresses the strap 392 against the tip and the slot 352 to provide resistance to pulling the strap 392. When the end 394 of the strap 392 is released, the elastic nature of the strap 392 causes the strap 392 to compress slightly, which causes the wedge 356 to rotate back in a counter-clockwise direction to its closed position. In use, the loop 396 may initially be made larger than the diameter of the distal end 44 of the endoscope so that the distal end 44 of the endoscope can be inserted into the loop 396. Thereafter, once the distal end 44 of the endoscope is positioned as desired with respect to the cap assembly 350, the strap(s) 392 can be pulled further through the slot 352 to tighten the strap(s) 392 against the endoscope to secure it to the mount 350.

Figure 16:
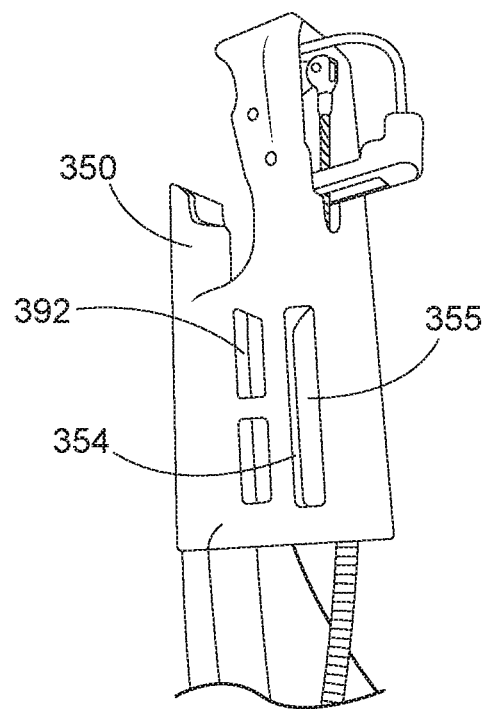
FIG. 16 is a view of the cap assembly of FIG. 14 shown with ends of straps trimmed.

The mount 350 also defines a strap trimming guide slot 354, and a blade guide 355 that define a blade pathway along which a cutting blade may pass at a fixed (or limited range) angle with respect to the direction of the strap slots 352 and any straps 392 in the respective slots. The guide slot 354 is configured to receive a knife blade (e.g., a scalpel) therethrough and the blade guide 355 is configured to act as a bearing surface against which the side of such knife blade abuts while the knife moves in the guide slot 354. In one embodiment, the strap trimming guide slot 354 defines a blade pathway that is substantially perpendicular to the direction of the strap slot 352 and straps 392. The guide slot 354 longitudinally extends across all of straps 392. The trimming guide slot 354 extends longitudinally so that the knife blade can be guided longitudinally (i.e., downwardly in FIG. 14) from one end of the slot to another end while being held at a relatively fixed angle with respect to the plane of the strap 392. The strap trimming guide slot 354 and blade guide 355 are configured to guide the knife in the slot 354 so that the knife blade can only be positioned at a fixed angle (or limited range of angles) with respect to the plane defined by the strap(s) 392. Thus, when a respective strap 392 is in its corresponding strap slot 352, the pathway of the strap trimming guide slot 354 intersects with the straps 392 so that a knife blade can be inserted at a fixed angle relative to the straps 392 defined by the slot 354 and the blade guide 355 to cut off the free ends 394 of the strap 392. FIG. 16 shows the straps 392 that have been trimmed. The trimming guide slot 354 prevents cutting the straps 392 too short, which could cause the straps to loosen during use, or too long, which could interfere with the movement of the endoscope during use.

Figure 17:
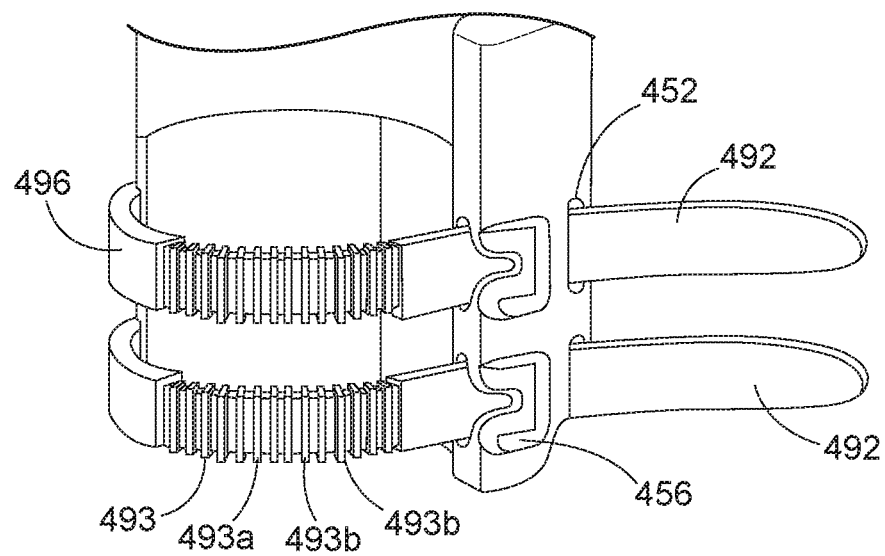
FIG. 17 is a partial view of another embodiment of a cap assembly.

FIG. 17 shows a variation of the embodiment shown in FIGS. 14 to 16, where the straps and strap retention arrangement are modified as follows. The straps 492 are configured to have a toothed or grooved outer surface 493. The mount 450 has a strap slot 452 bordered by one or more retention tabs 456. Each retention tab 456 has a tooth (not shown) extending into the slot 452. The slot 452 is configured to receive a corresponding strap 492. Each tab 456 is configured to engage the outer surface 493 of the strap 492 when the strap 492 is pulled through the slot 452, as shown in FIG. 17. Specifically, the tooth of the retention tab 456 is configured to engage spaces 493a between teeth 493b of the straps 492. As the teeth 493b of the strap 492 moves past the tooth of the retention tab 456, the retention tab 456 engages and releases (i.e., indexes) with each tooth 493b of the strap 492, similar to a zippered cable tie closure. The tooth of the retention tab 456 is configured so that it only readily permits the strap 492 to be tightened, but not loosened, again, similar to zippered cable tie closures. This one-way arrangement can be overcome by prying (e.g., with a special tool, not shown) the retention tab 456 and its tooth radially away outward) from the slot 452 out of engagement with the outer surface 493 of the strap 492. The distal end 44 of the endoscope can be placed within a loop 496 and the loop 496 can be tightened against the endoscope by pulling further on the straps 492.

Figure 18:
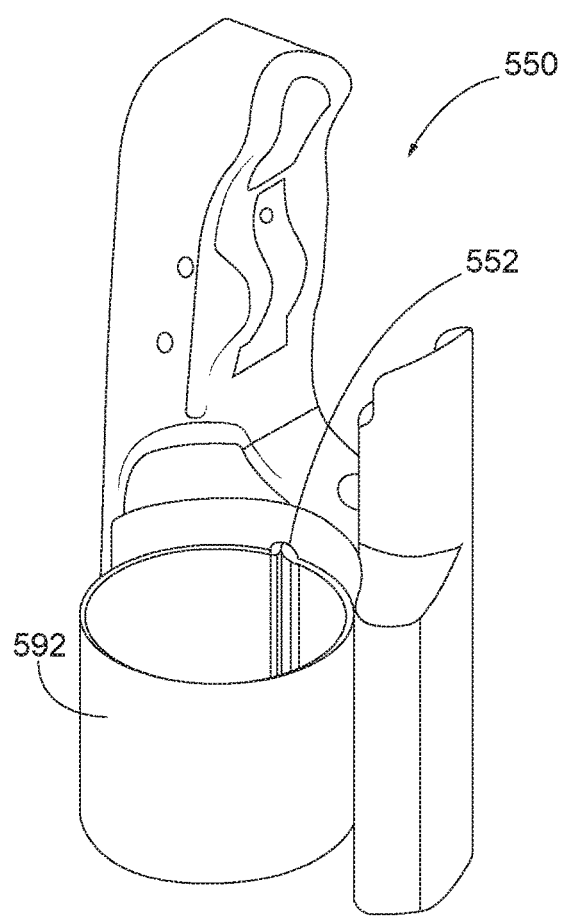
FIG. 18 is a distal end view of another embodiment of a cap assembly that is configured for attachment at the distal end of an endoscope of the endoscope suturing system.

FIG. 18 shows another variation of the embodiment of cap apparatus shown in FIGS. 14 to 16. In the embodiment shown in FIG. 18 a single strap 592 is used in place of the two straps 492 in FIGS. 14 to 16. Also, in FIG. 18, the mount 550 defines a single strap slot 552 in place of the two strap slots 352 in FIGS. 14 to 16. An embodiment using two straps may be preferable over a single strap made from the same material since multiple smaller multiple straps may be easier to individually tighten (require less force to pull) than a single larger strap.

Figure 19:
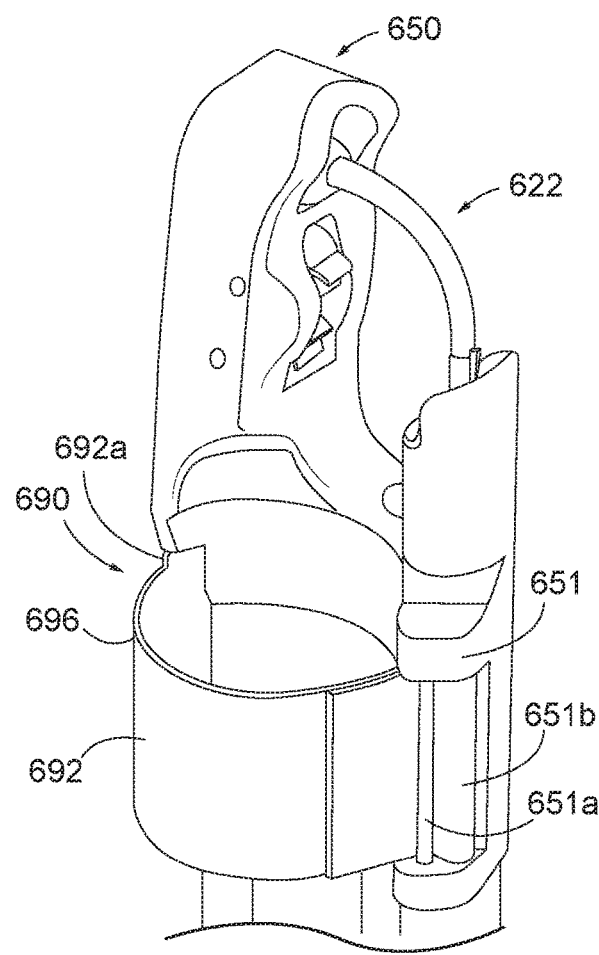
FIG. 19 distal end view of another embodiment of a cap assembly that is configured for attachment at the distal end of an endoscope of the endoscope suturing system.

Turning now to FIG. 19, another embodiment of a suturing system 622 is shown that is similar to suturing system 22 described above, but which includes variations on the cap apparatus. In distinction from the cap clip 90 with resilient arm 94 of the earlier embodiment, the suturing system 622 includes a cap apparatus 690 defined by at least one strap 692 that is structured to retain the distal end 44 (not visible in FIG. 19) of the endoscope adjacent a cap mount 650. The strap 692 is preferably elastic and may be formed from silicone rubber or similar material.

The cap mount 650 defines a notch 651 in which is disposed a pair of rods 651a and 651b. The strap 692 is secured at one end to the cap mount 650 and an opposite end 694 of the strap 692 is routed around rod 651b and between rods 651b and 651a so that a loop 696 of the strap 692 can be formed in which the distal end 44 of the endoscope can be received. The spacing and relative position between the rods 651a and 651b are configured to compress against the strap 692 and prevent the strap 692 from being loosened once the strap 692 is tightened. Also, the strap 692 is formed of a material that will not loosen after the strap 692 is tightened. The loop 696 can be preformed before inserting the distal end of the endoscope into the loop 696, after which the end 694 of the strap 692 can be pulled further to tighten the loop 696 to secure the endoscope to the cap mount 650.

Figure 20:
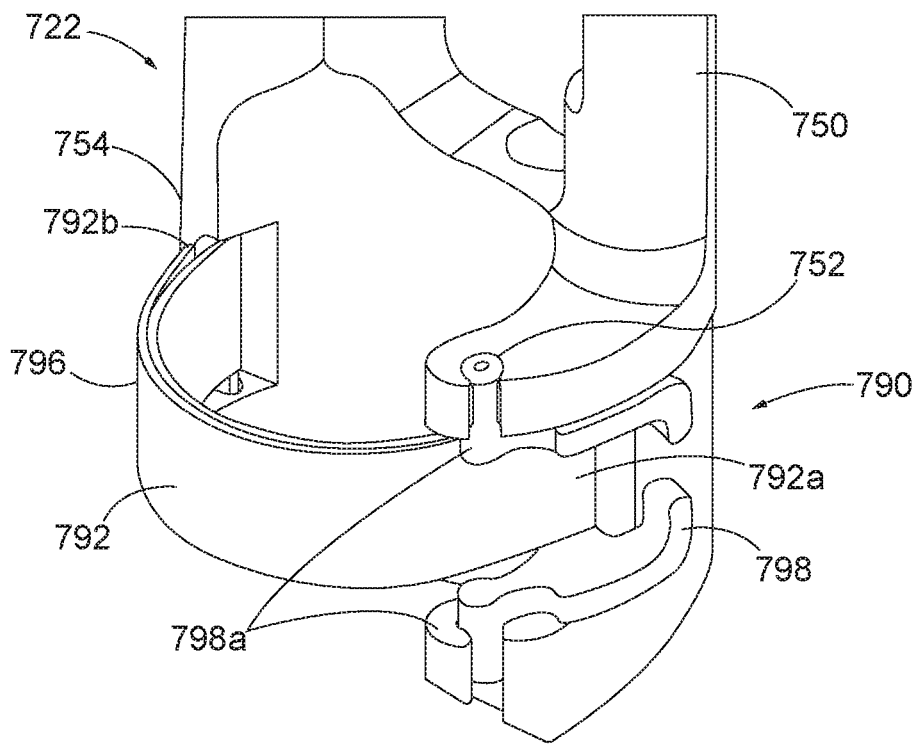
FIG. 20 is a partial view of another embodiment of a cap assembly.

Turning now to FIG. 20, another embodiment of a suturing system 722 is shown that is similar to suturing system 22 described above, but which includes variations on the peripheral engagement structure. In distinction from the cap clip 90 with resilient arm 94 of the earlier embodiment, the suturing system 722 includes a cap apparatus 790 defined by at least one strap or band 792 that is structured to retain the distal end 44 (not visible in FIG. 20) of the endoscope adjacent the cap mount 750. The strap or band 792 is preferably elastic and may be formed from silicone rubber or similar material. In the embodiment shown in FIG. 20 a continuous elastic band 792 is shown.

The engagement structure 790 also includes a buckle 798 that is coupled to an end 792a of the band 792. The buckle 798 has a set of pins 798a that are pivotally coupled to a hinge 752 formed in the cap mount 750. An opposite end 792b of the band 792 is coupled to the cap mount 750 by a pin 754. The buckle 798 is configured to move between an open and a closed position (shown in FIG. 20) to operatively clamp down on the distal end 44 of the endoscope. As shown in the closed position in FIG. 20, an outer surface of the buckle 798 is flush with an outer surface of the cap mount 750. The buckle 798 can be rotated about the hinge 752 (clockwise in FIG. 20) to open the buckle 798, which loosens the band 792 so that the distal end 44 of the endoscope can be positioned in a loop 796 defined between the band and the curved surface of the cap mount 750. When the distal end 44 of the endoscope is located in a desired orientation in the loop 796, the buckle 798 can be moved to its closed position, which will tighten or clamp down the band 792 around the endoscope to secure the it against the cap mount 750 in the desired orientation.

Figure 21:
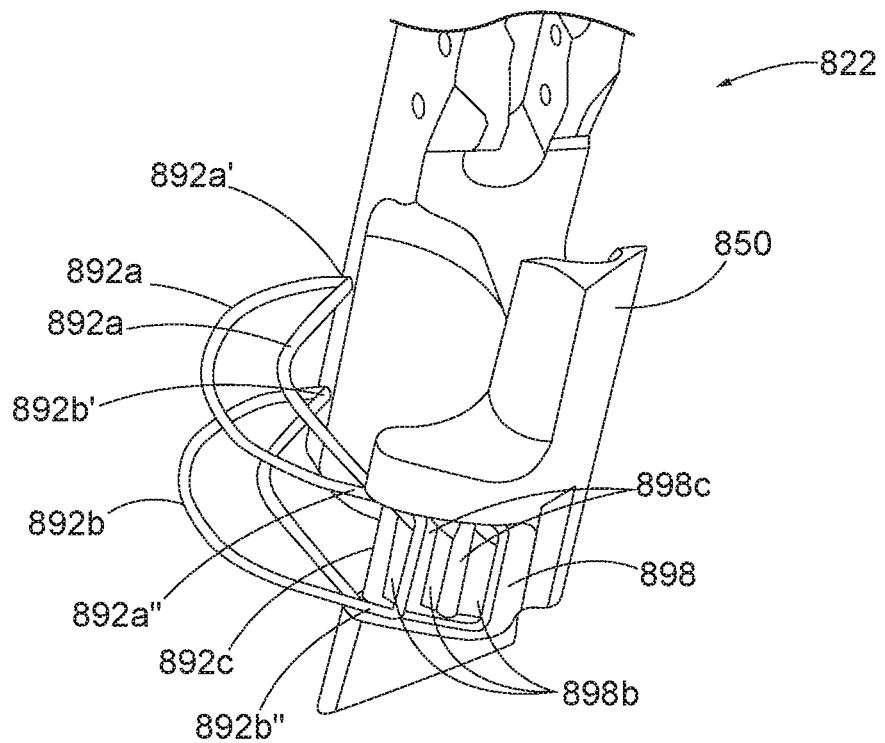
FIG. 21 is a partial view of another embodiment of a cap assembly.

Turning now to FIG. 21, another embodiment of a suturing system 822 is shown that is substantially similar to suturing system 22 described above, but which includes variations on the peripheral engagement structure. In distinction from the cap clip 90 with resilient arm 94 of the earlier embodiment, the suturing system 822 includes a cap apparatus 890 defined by at least one strap or band 892 that is structured to secure the distal end 44 (not visible in FIG. 21) of the endoscope adjacent the cap mount 850. The strap or band 892 may be elastic and may be formed from silicone rubber or similar material. The strap or band 892 may be formed as a resilient cord or "bungee". In the embodiment shown in FIG. 2 an upper set of elastic bands 892a and a lower set of elastic bands 892b are shown in their neutral, undeformed (relaxed) state. Each set of bands 892a and 892b are configured the same with an outer band of larger circumferential length and an inner band of relatively smaller circumferential length. The inner and outer bands of each set of bands may be joined together forming a continuous looped band, like the looped band 792 of FIG. 20. The upper bands 892a and the lower bands 892b are secured at their respective ends 892a' and 892b' to the cap assembly 850. The upper band 892a and the lower band 892b are secured at respective ends 892a" and 892b" to a pin 892c.

The engagement structure 890 also includes a buckle 898 that is hingedly coupled to the cap mount 850. The buckle 898 has a plurality of teeth 898b separated by grooves 898c that are configured to selectively receive the pin 892c in one of the grooves. The buckle 898 is configured to move between an open and a closed position (shown in FIG. 21). As shown in FIG. 21, in the closed position, an outer surface of the buckle 898 is generally flush or parallel with the outer surface of the cap mount 850. The buckle 898 can be rotated about its hinged connection clockwise in FIG. 21 to open the buckle 898, which loosens the bands 892a and 892b. When the buckle 898 is opened, the pin 892c can be positioned in one of the grooves 898c and the buckle 898 can then be closed. The selection of a specific groove 898c depends on the size of the endoscope to be clamped and the amount of force to be applied by the bands 892a and 892b. When the buckle is opened, the distal end 44 of the endoscope can be located in a desired position between the bands 892a and 892b and the mount 850. The pin 892c can then be positioned in the groove 898c that places the inner bands 892a and 892b in closest proximity (or in contact) with the endoscope. When the pin 892c is so positioned, the buckle 898 can be rotated into its closed position to tighten or clamp down the bands 892a and 892b on the endoscope to secure the endoscope against the cap mount 850.

The suturing assemblies described above are adapted for use with an endoscope that does not necessarily have at least two instrument channels. As such, the suturing system can be used smaller endoscopes that are available in many surgical setting and which can be more easily advanced through a natural orifice.

There have been described and illustrated herein embodiments of a suturing system as well as a surgical treatment system, as well as methods of using the same. While particular embodiments of the invention have been described, it is not intended that the invention be limited thereto, as it is intended that the invention be as broad in scope as the art will allow and that the specification be read likewise. Thus, while particular instruments and devices for advancement through the first and second lumen have been disclosed, it will be appreciated that other instruments can also be used through such lumen for like or even different purpose. Also, while the treatment system has been particularly described with respect to a cap assembly having an end effector in the form of a needle arm that carries a needle, it is recognized that alternatively one or more movable end effectors with other structure and purpose can be provided to the cap assembly. Also, while a tissue anchor in the form of a needle assembly has been described, the end effector can deploy different types of tissue anchors, including, e.g., clips. In addition, while a particular needle assembly has been described, other needle assemblies can similarly be used. Also, the size and instrument channel features of the endoscope with which the system is used is not critical, it is appreciated that various prior art systems cannot be properly used in a suturing operation in conjunction with endoscopes having fewer than two instrument channels, one for receiving a needle exchange device and the other for receiving a tissue retractor, whereas the present system is capable of complete operation without the provision of any channels through the endoscope. It will therefore be appreciated by those skilled in the art that yet other modifications could be made to the provided invention without deviating from its scope as claimed.

What is claimed is:

1. A distal cap apparatus for use with an endoscope having a proximal end and a distal end and a longitudinal axis extending therebetween, comprising:
    a mount configured for mounting to the distal end of the endoscope;
    a strap having first and second ends and a length extending therebetween, said strap being connected to the mount at the second end of the strap,
    the strap having a loop configuration for banding about the distal end of the endoscope when the distal end of the endoscope is received in the mount to retain the mount on the endoscope,
    wherein the mount defines,
    a) a strap slot configured to receive the first end of the strap and retain the first end of the strap to configure the strap in a loop with a size to position the endoscope within the loop and allow the first end to be pulled through the strap slot to tighten the strap against the endoscope, and
    b) a straight cutting blade slot extending longitudinally in a direction intersecting with a pathway through which the strap extends, the cutting blade slot adapted to accommodate a cutting blade to sever a portion of the strap between the first and second ends of the strap.

2. The apparatus according to claim 1, wherein:
the strap is elastic.

3. The apparatus according to claim 1, wherein:
the strap slot is dimensioned to compress the strap when the strap is in the strap slot.

4. The apparatus according to claim 1, wherein:
the strap is frictionally engaged in the strap slot to retain the strap positioned relative to the strap slot.

5. The apparatus according to claim 1, wherein:
the mount defines a blade bearing surface extending in a plane at a fixed angle that intersects with a plane of the strap in the strap slot to allow the cutting blade to be received within the cutting blade slot, bear against the strap at the fixed angle of the blade bearing surface, and sever a portion of the strap extending through the cutting blade strap slot.

6. The apparatus according to claim 5, wherein:
the blade bearing surface is a portion of the cutting blade slot.

7. The apparatus according to claim 1, wherein:
the mount has a locking tab that extends into the strap slot and is configured to engage with the strap when the strap is in the strap slot; and
the strap has a plurality of teeth and grooves that engage the locking tab when the strap is moved through the strap slot.

8. The apparatus according to claim 7, wherein:
the locking tab is configured to permit the strap to move in only one direction through the strap slot.

9. The apparatus according to claim 1, wherein:
the cutting blade slot is positioned to receive the cutting blade so that the cutting blade is located to sever the strap after the strap is received in the strap slot.

* * * * *